(12) United States Patent
Guerin

(10) Patent No.: US 6,997,963 B2
(45) Date of Patent: Feb. 14, 2006

(54) USE OF A CHROMOIONOPHORE AND/OR FLUOROIONOPHORE FOR DYEING HUMAN KERATIN FIBRES, DYEING COMPOSITIONS AND METHODS

(75) Inventor: Frederic Guerin, Paris (FR)

(73) Assignee: L'Oreal, (FR)

( * ) Notice: Subject to any disclaimer, the term of this patent is extended or adjusted under 35 U.S.C. 154(b) by 327 days.

(21) Appl. No.: 10/607,506

(22) Filed: Jun. 27, 2003

(65) Prior Publication Data

US 2005/0074419 A1    Apr. 7, 2005

Related U.S. Application Data

(60) Provisional application No. 60/393,748, filed on Jul. 8, 2002.

(30) Foreign Application Priority Data

Jun. 28, 2002    (FR) .................................. 02 08145

(51) Int. Cl.
C09B 69/10    (2006.01)
A61K 7/13    (2006.01)
(52) U.S. Cl. ...................... 8/647; 8/405; 8/406; 8/408; 8/410; 8/411; 8/421; 8/426; 8/435; 8/552; 8/626; 8/628; 424/70.6
(58) Field of Classification Search .................. 8/647, 8/405, 406, 408, 410, 411, 421, 426, 435, 8/552, 626, 628; 424/70.6
See application file for complete search history.

(56) References Cited

U.S. PATENT DOCUMENTS 4,367,072 A    1/1983    Vogtle et al. ................ 436/501
6,306,182 B1 *    10/2001    Chan et al. .................... 8/426

FOREIGN PATENT DOCUMENTS

| EP | 0 594 047 | 4/1994 |
| EP | 0 826 677 | 3/1998 |
| WO | WO 94/04539 | 3/1994 |

OTHER PUBLICATIONS

Buschmann, H.J., et al, "Ionenselektive Farbstoffe zum Farben von Polyamid," Chemiefasem/Textilindustrie, vol. 40, No. 5, May 1990, pp. 449-452.

* cited by examiner

Primary Examiner—Eisa Elhilo
(74) Attorney, Agent, or Firm—Steptoe & Johnson LLP

(57) ABSTRACT

The present invention concerns a dye composition for dyeing human keratin fibres such as hair containing, in an appropriate medium for dyeing human keratin fibres, at least one compound chosen from among chromoionophores and fluorionophores, and at least one cosmetic additive other than water. The invention also concerns the use of a compound chosen from among the chromoionophores and fluorionophores as a direct dye for dyeing human keratin fibres, methods for dyeing human keratin fibres and a device or "kit" with several compartments.

52 Claims, No Drawings

USE OF A CHROMOIONOPHORE AND/OR FLUOROIONOPHORE FOR DYEING HUMAN KERATIN FIBRES, DYEING COMPOSITIONS AND METHODS

The present application claims priority under 35 U.S.C. § 119(e) to U.S. Provisional Application Ser. No. 60/393,748, filed Jul. 8, 2002.

The present invention concerns the area of dyeing human keratin fibres such as hair. More particularly, it relates to the use of a compound chosen from among the chromoionophores and fluorionophores as a direct dye for dyeing human keratin fibres, to a dye composition for dyeing human keratin fibres containing, in an appropriate medium, at least one of the compounds and at least one cosmetic additive, to methods for dyeing the fibres and to a device with several compartments for dyeing the fibres.

For dyeing keratin fibres, human hair in particular, dye compositions are known to be used containing precursors of oxidation dyes, generally called oxidation bases, such as ortho- or para-phenylenediamines, ortho- or para-aminophenols and heterocyclic compounds. These oxidation bases are colourless or scarcely coloured compounds which, when associated with oxidizing products, give rise to coloured compounds via an oxidative condensation process.

It is also known that the shades obtained with these oxidation bases can be varied by combining them with colouring couplers or modifiers, the latter being especially chosen from among the aromatic metadiamines, meta-aminophenols, metadiphenols and some heterocyclic compounds such as indole compounds.

With the variety of molecules involved in oxidation bases and couplers, a rich palette of colours can be obtained.

This oxidation dye method consists of applying to keratin fibres either oxidation bases or a mixture of oxidation bases and couplers with an oxidizing agent, hydrogen peroxide for example, leaving them on for a certain length of time and then rinsing the fibres. The resulting colouring is permanent, powerful and resistant to outside agents, in particular light, adverse weather conditions, washings, perspiration and friction.

Direct dyeing is also known for dyeing keratin fibres. The conventional method used for direct dyeing consists of applying direct dyes to keratin fibres, which are coloured, colouring molecules having an affinity for the fibres, leaving them on for awhile, then rinsing the fibres. The use is known for example of nitrobenzene, anthraquinone, nitropyridine, azoic, xanthene, acridine, azine or triarylmethane direct dyes.

The resulting colour is particularly chromatic but temporary or semi-permanent on account of the type of bonds between the direct dyes and keratin fibres. These interactions lead to easy desorption of the dyes from the surface and/or the core of the fibre.

With these hair colouring products, it is possible to change hair colour for some weeks or months. However, it may also be of advantage to change hair colour for some days or even for some hours and to have the initial colour restored without impairing fibre integrity.

The objective of the present invention is to provide new dye compositions for dyeing human keratin fibres which makes it possible to obtain chromatic colouring with homogeneous light reflection, which is resistant and glossy, and which can subsequently be easily modified without the addition of another dye.

In advantageous, unexpected manner, the applicant has found that it is possible to attain this objective by using as direct dye, in a medium appropriate for dyeing human keratin fibres, at least one compound chosen from among the chromoionophores and fluoroionophores.

With the dye compositions of the invention, it is possible to obtain a colour which may be subsequently changed for a few hours, a few days, a few weeks or a few months. The user can therefore choose a colour, change it to a second colour, then choose to come back to the initial colour or to maintain the second colour, without the colour changes leading to subsequent hair impairment.

It is therefore possible according to the invention to modulate the colour of the chromo-ionophores/fluoroionophores before or after application to keratin fibres.

These compositions of the invention make it possible to achieve particularly chromatic colours. They can be used to dye only a few locks of hair or the entire head of hair.

The dyes obtained with the dye compositions of the invention are resistant to adverse weather conditions, washings and perspiration. In addition, the chromo-ionophores and fluorionophores are sufficiently stable in the presence of oxidizing and reducing agents to allow fibre lightening either through the use of direct lightening compositions containing the same, or through the use of oxidation dye compositions containing the same. These chromoionophores and fluoroionophores can be used to dye keratin fibres over a very wide range of highly chromatic colours, without omitting so-called "basic" shades such as blacks or browns.

The chromoionophores and fluoroionophores are compounds made up of one or more ionophore molecules bound covalently to at least one molecule chosen from among the chromophores and fluorophores, the molecule chosen from the chromophores and fluorophores preferably being a direct dye.

One first subject of the invention is the use as direct dye in or for the manufacture of compositions for dyeing human keratin fibres, hair in particular, of at least one compound chosen from among the chromoionophores and fluoroionophores, this compound being made up of at least one ionophore molecule covalently bound to at least one molecule chosen from among the chromophores and fluorophores.

A second subject of the present invention is a dye composition for dyeing human keratin fibres, hair in particular, containing, in an appropriate medium for dyeing keratin fibres, at least one compound chosen from among the chromoionophores and fluoroionophores, and at least one cosmetic additive other than water. The cosmetic additive may in particular be chosen from among anionic, cationic, nonionic, amphoteric or zwitterionic surfactants or their mixtures, anionic, cationic, nonionic, amphoteric or zwitterionic polymers or their mixtures, mineral or organic thickening agents, in particular anionic, cationic, nonionic and amphoteric associative polymers, antioxidant agents, penetration agents, sequestering agents, perfumes, dispersing agents, conditioning agents such as volatile or non-volatile silicones for example, whether modified or non-modified, fats including ceramides and fatty alcohols, preservation agents, and opacifying agents.

"Conditioning agent" in the present application denotes a compound able to improve the cosmetic properties of keratin fibres, such as untangling, feel, smoothing, shine and volume.

A chromophore is a compound which absorbs in the visible; therefore, this compound is coloured. Among conventional chromophores, it is therefore those having the property of being dyes able to dye human keratin fibres which are preferably used within the scope of this application.

In the present application, a fluorophore is intended to mean a compound which absorbs in the ultraviolet and visible domains; therefore, this compound is coloured. Among conventional fluorophores, it is therefore those having the property of being dyes able to dye human keratin fibres which are preferably used within the scope of the present invention.

In preferred manner, the molecule chosen from among the chromophores and fluorophores is a direct dye whether or not containing at least one cycloaliphatic, aromatic or heterocyclic cycle. In addition, the direct dye does not contain more than four condensed cycles.

These dyes are particularly chosen from among conventional direct dyes. They are aromatic or non-aromatic molecules chosen from the group made up of neutral, acid or basic direct nitrobenzene dyes, neutral, acid or basic direct azoic dyes, neutral, acid or basic direct quinone dyes, anthraquinone in particular, direct azine dyes, direct methine dyes such as neutral, acid or basic methines and azomethines, direct triarylmethane dyes, direct indoamine dyes, direct natural dyes such as carotenoids, terpenoids, flavonoids, porphyrins, fluoresceine, rhodamine, and coumarines.

Ionophores are molecules able to complex ions.

In the scope of the present invention, all ionophores may be used to form the compound chosen from the chromoionophores and fluoroionophores. The iono-phore molecules(s) are usually chosen from among open-structure molecules such as chelatants or podands, macrocycles called ether-crowns or coronands, and macrobicycles called cryptands.

In the present application, "podands" denote open-structure molecules able to complex ions in which the complexing part is a chain containing heteroatoms. These molecules are oligoethers, for example. The article "Chromo- and Fluoroionophores—A new class of dye reagents, " ACC. CHEM. RES., 1985, 18, 65–72, page 69 et seq., describes podand compounds which may be used within the scope of this invention.

In the present application, "cooronand" means bi-dimensional, closed-structure molecules able to complex ions. Generally, these are hydrocarbon monocyclic molecules containing heteroatoms. These molecules are macrocyclic polyethers for example containing the pattern:

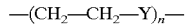

where Y is a heteroatom chosen from among O, S, N and P and n is an integer greater than 2 preferably lying between 4 and 10.

These molecules are crown ethers for example such as 15-crown-5, 18-crown-6; crown benzo-ethers such as benzo- 15-crown-5, benzo- 18-crown-6, dibenzo- 15-crown-5, dibenzo- 18-crown-6; crown monoaza-ethers or crown diaza-ethers such as aza-15-crown-5, aza-18-crown-6, diaza-15-crown-5, and diaza-18-crown-6.

The crown ethers contain the following pattern:

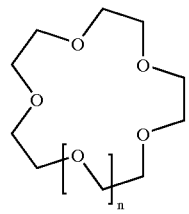

in which n is an integer from 0 to 10.

The monoaza- and diaza-crown ethers contain the following patterns:

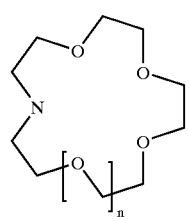 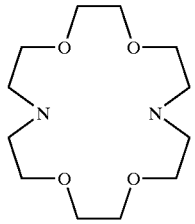

in which n is an integer from 0 to 10.

In the present application, "cryptands" denote three-dimensional, closed-structure molecules (cages) able to complex ions. Generally, they are hydrocarbon bicyclic molecules containing heteroatoms. These molecules are macrobicyclic polyethers for example containing the pattern:

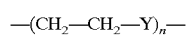

where Y is a heteroatom chosen from among O, S, N and P and n is an integer greater than 2 preferably lying between 2 and 10.

The macrobicyclic polyethers have the following general structure:

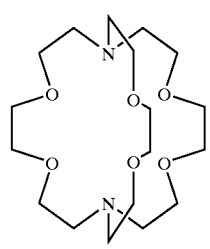

The fixing of the ionophore molecule(s) on the molecule(s) chosen from among the chromophores and fluorophores is preferably made by one or more simple covalent bonds. However, this fixing may also be achieved using one or more divalent radicals such as alkylene radicals (methylene, ethylene, propylene, and butylene for example) or aromatic or heterocyclic divalent radicals.

Fixing may be made using one or more atoms of the ionophore molecule (carbon atoms or heteroatoms).

All conventional chemical reactions can be used to prepare the compounds chosen among the chromoionophores and fluoroionophores using an ionophore molecule and one or more molecules chosen from among the chromophores and fluorophores.

Some chromoionophores or fluoroionophores are products known in themselves such as those listed in the table below for example:

| Structure | CAS |
|---|---|
| 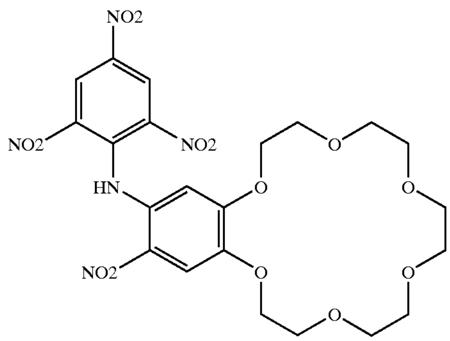 | 74305-50-3 |
| 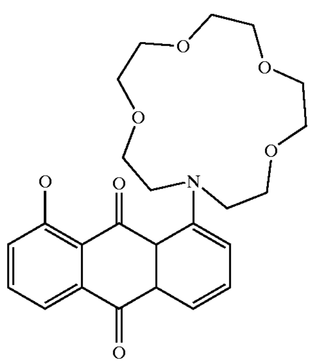 | 77101-97-4 |
| 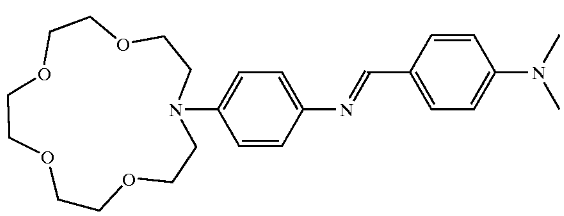 | 361454-18-4 |
| 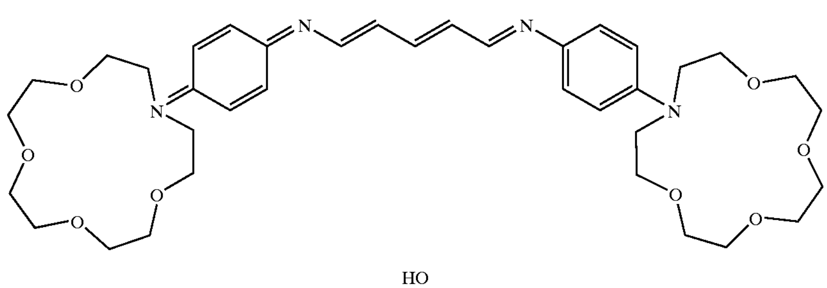 | 73171-31-0 |

| Structure | CAS |
|---|---|
| 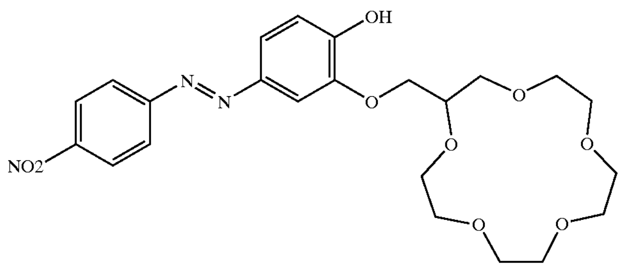 | 81760-15-8 |
| 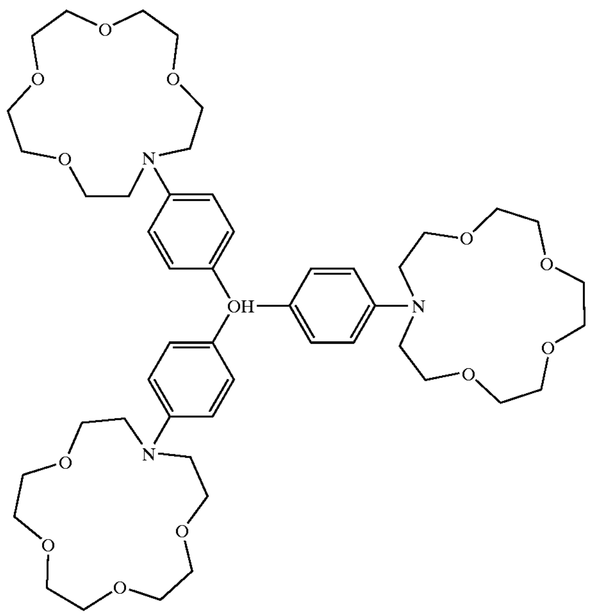 | 66749-97-1 |
| 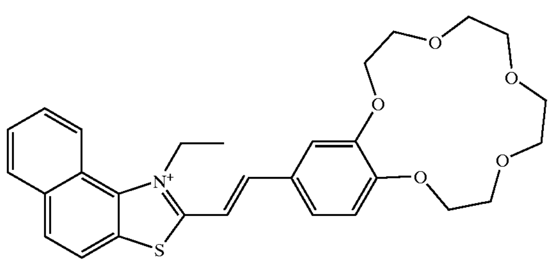 | 174542-39-3 |

Generally, the compound or compounds chosen from among the chromoionophores and fluoroionophores are used in a concentration ranging from approximately 0.0001 to 20% by weight relative to the total weight of the composition, preferably from 0.0001 to 10% and more particularly from 0.0001 to 5%.

The dye composition of the present invention may be used to dye human keratin fibres, hair in particular, in a colour chosen by the user which can then be modified by simply adding an ionic compound possibly also being a cosmetic additive. These ionic compounds may be present in the composition of the invention or in another composition directly applied to the human keratin fibres.

Without seeking to be bound by any theory, it would appear that the addition of ions in the environment of chromoionophore and/or fluoroionophore molecules makes it possible to modify the absorption spectrum of these molecules by electron delocalisation, of which the consequence is a change in the colour of the chromoionophore and/or fluoroionophore molecules.

The ions which may be used according to the present invention may be cations or anions. Preferable use is made of cations in salt form.

The salts used are physiologically acceptable salts of inorganic or organic type.

Among the inorganic salts, metal salts are preferred, further preference being given to inorganic salts of alkaline metals, alkaline-earth metals, transition metals, rare earth metals and their alloys.

Alkaline metals may be chosen from among lithium (Li), sodium (Na), potassium (K) and caesium (Cs).

Alkaline-earth metals may be chosen from among beryllium (Be), magnesium (Mg), calcium (Ca), strontium (Sr) and barium (Ba).

The transition metals may be chosen in the series of elements ranging from scandium (Sc) to zinc (Zn) such as listed in the periodical table of elements, i.e., among the following elements: Sc, Ti, V, Cr, Mn, Fe, Co, Ni, Cu and Zn in the series ranging from Yttrium (Y) to cadmium (Cd), i.e., among the following elements: Y, Zr, Nb, Mo, Tc, Ru, Rh, Pd, Ag, and Cd; or the lanthanum series (La), i.e., among the following elements: La, Hf, Ta, W, Re, Os, Ir, Pt, and Au.

The preferred salts of heavy metals are physiologically acceptable salts of zinc, lead, calcium, copper, manganese, iron, cobalt, nickel, tin, silver or magnesium, in the form of chloride, sulphate, nitrate or acetate salts.

The rare earth metals may be chosen in the series of elements of lanthanide type, from cerium (Ce) to lutetium (Lu), i.e., among the following elements: Ce, Pr, Nd, Pm, Sm, Eu, Gd, Tb, Dy, Ho, Er, Tm, Yb, and Lu.

In the compositions of the invention therefore the corresponding salts of nitrate, sulphate, carbonate, halogenide, bromate, phosphate, sulphonate, acetate, and chloride type will be used.

Among the organic salts, preference is given to ammonium salts such as benzyltrimethylammonium, isobutylammonium, butyltrimethylammonium, decyltrimethylammonium, diethylammonium, dimethylammonium, such as laccases. The use of hydrogen peroxide is particularly preferred.

The composition of the invention may also contain at least one oxidation base. This oxidation base may be chosen from among conventionally used oxidation bases for oxidation dyeing, for example the para-phenylenediamines, bisphenylalkylenediamines, para-aminophenols, ortho-aminophenols and heterocyclic bases.

The quantity of oxidization base or bases present preferably lies between approximately 0.001 and 10% by weight of the total weight of the dye composition, and more preferably between 0.005 and 6%.

The composition of the invention may also contain one or more couplers conventionally used for dyeing keratin fibres. Among such couplers the following are particularly cited: metaphenylenediamines, meta-aminophenols, metadiphenols, naphthalene couplers and heterocyclic couplers.

In the composition of the present invention, the coupler or couplers are generally present in a quantity ranging from approximately 0.001 to 10% by weight of the total weight of the dye composition, and more preferably from 0.005 to 6%.

As a general rule, the addition salts with an acid which may be used in the dye compositions of the invention for the oxidation bases and couplers are especially chosen from among the hydrochlorates, hydrobromates, sulphates, citrates, succinates, tartrates, lactates, tosylates, benzene-sulphonates, phosphates and acetates. dipropylammonium, dodecylammonium, dodecyltrimethyl-ammonium, ethanolammoniumn, ethylammonium, ethyltri-methylammonium, and diammonium salts.

The ionic compound or compounds are preferably present in a weight concentration lying between 0.001 to 25%, preferably from 0.01 to 10%, and more preferably from 0.1 to 5%, relative to the total weight of the composition.

The composition of the present invention may also contain at least one additional direct dye.

This additional direct dye may be chosen from among neutral, acid or cationic direct nitrobenzene dyes, neutral acid or cationic direct azoic dyes, direct quinone dyes and in particular neutral, acid or cationic anthraquinone dyes, direct azine dyes, direct methine dyes, direct triarylmethane dyes, direct indoamine dyes and direct natural dyes.

The additional direct dye or dyes preferably represent from approximately 0.001 to 20% by weight of the total weight of the composition, and more preferably between approximately 0.005 and 10% by weight.

The composition of the invention may also contain an oxidizing agent. This oxidizing agent may be any oxidizing agent conventionally used for decolouring keratin fibres. The oxidizing agent is preferably chosen from among hydrogen peroxide, urea peroxide, alkaline metal bromates, persalts such as perborates and persulfates, peracids and enzymes among which mention may be made of peroxidases, 2-electron oxy-reductases such as uricases, and 4-electron oxygenases The appropriate dye medium, also called dye carrier, is generally formed of water or a mixture of water and at least one organic solvent. As organic solvent, the lower $C_1$–$C_4$ alcohols may be cited for example such as ethanol and isopropanol; the polyols and polyol ethers such as 2-butoxyethanol, propyleneglycol, the monoethylether of propyleneglycol, the monoethylether and monomethylether of diethyleneglycol, and the aromatic alcohols such as benzyl alcohol or phenoxyethanol, and their mixtures.

The organic solvents may be present in proportions preferably lying between approximately 1 and 40% by weight relative to the total weight of the dye composition, and more preferably between approximately 5 and 30% by weight.

In the dye composition of the invention, the above-cited additives are generally present in quantities ranging for each one from 0.01 to 20% by weight relative to the weight of the composition.

Evidently, persons skilled in the art shall ensure that this or these possible additional compounds are chosen such that the advantageous properties intrinsically attached to the dye composition of the invention are not, or not substantially, impaired by the considered addition or additions.

The pH of the dye composition of the invention generally lies between approximately 3 and 12, preferably between 5 and 11. It may be adjusted to the desired value using acidifying or alkalinising agents usually used for dyeing keratin fibres or even using conventional buffer systems.

Among the acidifying agents, as examples the mineral or organic acids may be cited such as hydrochloric acid, orthophosphoric acid, sulphuric acid, and the carboxylic acids such as acetic acid, tartaric acid, citric acid, lactic acid, and sulphonic acids.

As examples of alkalinising agents, mention may be made of ammonia, alkaline carbonates, alkanolamines such as mono- di- and triethanolamines and their derivatives, the hydroxides of sodium or potassium and compounds having the following formula (III):

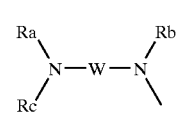

(III)

where W is a propylene remainder optionally substituted by a hydroxyl group or a $C_1$–$C_4$ alkyl radical: Ra, Rb, Rc and Rd, identical or different, representing a hydrogen atom, a $C_1$–$C_4$ alkyl radical or $C_1$–$C_4$ hydroxyalkyl.

The dye composition may be in various forms, such as liquid, cream, gel form or any other appropriate form to produce a dye for keratin fibres, human hair in particular.

A third subject of the present invention is a method for dyeing human keratin fibres, hair in particular, which comprises the application to human keratin fibres of a composition containing at least one compound chosen from among the chromoionophores and fluoroionophores for a sufficient length of time to develop the desired colouring. The fibers are then rinsed and dried.

In this method, the composition may also contain a cosmetic additive other than water which may in particular be chosen from among anionic, cationic, non-ionic, amphoteric, zwitterionic surfactants or their mixtures, anionic, cationic, nonanionic, amphoteric or zwitterionic polymers or their mixtures, mineral or organic thickening agents, in particular anionic, cationic, nonionic and amphoteric associative polymers, antioxidant agents, penetration agents, sequestering agents, perfumes, dispersing agents, conditioning agents such as volatile or non-volatile silicones for example, whether modified or non-modified, fats including ceramides and fatty alcohols, preservative agents, and opacifying agents.

One variant of the invention consists of including at least one ionic compound in the composition containing the chromoionophore or fluoroionophore compound or compounds.

The ionic compounds may be present in a composition containing the chromoionophore(s) or fluoroionophore(s) that is stored before use; they may also be present in a second composition which is added, at the time of use, to the composition containing the chromoionophore(s) or fluoroionophore(s).

A fourth subject of the present invention is a method for dyeing human keratin fibres, in several steps, one of these steps comprising the application of a composition containing at least one chromoionophore or fluoroionophore compound such as described above, the step being preceded or followed by the application of at least one composition containing at least one ionic compound.

The application of the two compositions may be separated by intermediate rinsing.

Preferably, the composition containing the ionic compound(s) is added onto the human keratin fibres after the compound chosen from among the chromoionophores and fluoroionophores is applied to these fibres. In this manner, the user may modulate his/her initial colour to greater or lesser extent through the gradual addition of ions.

Each of the applications lasts from 5 minutes to 1 hour, preferably from 10 to 30 minutes.

The ionic compound(s) are present in the dye compositions of the invention at a concentration ranging from approximately 0.001 to 25% by weight, preferably from approximately 0.01 to 10%, and more preferably from 0.1 to 5%, relative to the total weight of the composition.

The composition of the invention is generally applied at a temperature lying between room temperature and 80° C., preferably between 25° C. and 55° C.

A further subject of the invention is a direct hair lightening dye method which comprises the application to the fibres of a composition containing a compound chosen from among the chromoionophores and fluoroionophores in the presence of an oxidizing agent, which causes decolouring of the fibre. This oxidizing agent may be added to the composition containing the compound chosen from among the chromoionophores and fluoroionophores at the time of use or directly onto the keratin fibre.

A further subject of the invention is an oxidation dye method which comprises application to the fibres of a dye composition containing a compound chosen from among the chromoionophores and fluoroionophores, at least one oxidation base and optionally at least one coupler, in the presence of an oxidizing agent. The oxidation base, the coupler and oxidizing agent are such as defined above.

The colour may then be developed under acid, neutral or alkaline pH and the oxidizing agent may be added to the composition of the invention just at the time of use, or it may be contained in an oxidizing composition applied to the fibres simultaneously with or sequentially to the dye composition.

The pH of the oxidizing composition containing the oxidizing agent is such that after mixing with the dye composition, the pH of the resulting composition applied to the keratin fibres preferably varies between around 3 and 12, more preferably between 5 and 11. It may be adjusted to a desired value using acidifying or alkalinising agents usually used in kertain fibre dyeing as defined above.

The oxidizing composition may also contain various additives conventionally used in compositions for oxidation hair dyeing.

The pH of the oxidizing composition containing the oxidizing agent is such that after mixing with the dye composition, the pH of the resulting composition applied to the keratin fibres preferably varies between around 3 and 12, more preferably between 5 and 11. It may be adjusted to a desired value using acidifying or alkalinising agents usually used in keratin fibre dyeing as defined above.

The composition finally applied to the keratin fibres may be in various forms, such as liquid, cream, gel form or any other appropriate form for dyeing keratin fibres, human hair in particular. It may also be aerosol packaged in the presence of a propelling agent and form a mousse.

In similar fashion to a direct dyeing method, for the direct lightening dye method or oxidation dyeing, the application of the composition containing at least one compound chosen from among the chromoionophores and fluoroionophores may be preceded or followed by the application of a composition containing at least one ionic compound.

An additional subject of the present invention is a device in several compartments, or "kit" for dyeing human keratin fibres, hair especially. It comprises at least two compartments, of which one contains a composition containing, in an appropriate dye medium, at least one compound chosen from among the chromoionophores and fluoroionophores, and another contains a composition containing at least one ionic compound.

The following example illustrates the present invention but is not in any manner to be considered as limiting the invention.

The applicant produced the following composition according to the invention:

| | |
|---|---|
| Ionophore dye (*) at $10^{-3}$ mol % | 0.4 g |
| Laureth ether sodium sulphate | 0.1 g |
| Demineralised water | Up to 100 g |

The ionophore dye (*) has the following structure (MW = 414.5)

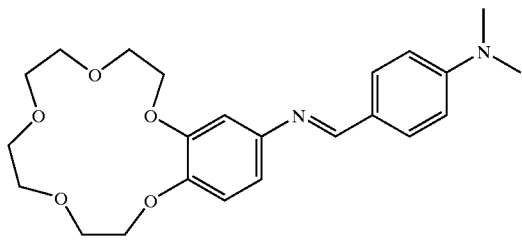

The dye composition obtained is applied to natural or permed grey hair, 90% grey, and left for 30 minutes.

After rinsing in running water and drying, the hair is dyed a fluorescent yellow shade.

What is claimed is:

1. A dye composition for dyeing human keratin fibres comprising, in a medium for dyeing human keratin fibres, at least one cosmetic additive other than water and at least one compound which is a chromoionophore or fluoroionophore, the compound being made up of at least one ionophore molecule covalently bound to at least one chromophore or fluorophore molecule.

2. The composition according to claim 1, wherein the chromophore or fluorophore molecule is a direct dye.

3. The composition according to claim 1, wherein the cosmetic additive is an anionic, cationic, nonionic, amphoteric or zwitterionic surfactant or mixture thereof, an anionic, cationic, nonionic, amphoteric or zwitterionic polymer or mixture thereof, a mineral or organic thickening agent, an antioxidant, a penetration agent, a sequestering agent, a perfume, a dispersing agent, a conditioning agent, a fat or fatty alcohol, a preservative agent, or an opacifying agent.

4. The composition according to claim 3, wherein the thickening agent is an anionic, cationic, nonionic or amphoteric associative polymer.

5. The composition according to claim 3, wherein the conditioning agent is a volatile or non-volatile silicone modified or unmodified.

6. The composition according to claim 3, wherein the fat is a ceramide.

7. The composition according to claim 1, wherein the chromophore or fluorophore is a molecule which is a neutral, acid or basic direct nitrobenzene dye, a neutral, acid or basic direct azoic dye, a direct quinone dye, a direct azine dye, a direct methine dye, a direct triarylmethane dye, a direct indoamine dye, or a direct natural dye.

8. The composition according to claim 7, wherein the quinone dye is a neutral, acid or basic anthraquinone dye.

9. The composition according to claim 7, wherein the methine dye is a neutral, acid or basic methine or azomethine.

10. The composition according to claim 7, wherein the natural dye is a carotenoid, terpenoid, flavonoid, porphyrin, fluorescein, rhodamin, or coumarin.

11. The composition according to claim 1, wherein the ionophore molecule is a chelatant, a podand, a coronand or a cryptand.

12. The composition according to claim 1, wherein the compound which is a chromoionophore or fluoroionophore is present at a concentration from 0.0001 to 20% by weight relative to the total weight of the composition.

13. The composition according to claim 12, wherein the concentration chromoionophore or fluoroionphore is from 0.001 to 10% by weight.

14. The composition according to claim 12, wherein the concentration chromoionophore or fluoroionphore is from 0.001 to 5% by weight.

15. The composition according to claim 1, wherein the medium for dyeing is water or a mixture of water and at least one organic solvent.

16. The composition according to claim 15, wherein the organic solvent is a lower $C_1$–$C_4$ alcohol, a polyol or polyol ether, an aromatic alcohol, or a mixture thereof.

17. The composition according to claim 1, wherein the composition further contains at least one ionic compound.

18. The composition according to claim 17, wherein the ionic compound contains at least one cation of a salt which is a physiologically acceptable organic or inorganic salt.

19. The composition according to claim 18, wherein the ionic compound is an inorganic metal salt which is an alkaline metal, an alkaline earth metal, a transition metal, a rare earth metal or an alloy thereof.

20. The composition according to claim 19, wherein the alkaline metal is Li, Na, K, or Cs.

21. The composition according to claim 19, wherein the alkaline earth metal is Be, Mg, Ca, Sr, or Ba.

22. The composition according to claim 19, wherein the transition metal is Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, or Au.

23. The composition according to claim 19, wherein the rare earth metal is Ce, Pr, Nd, Pm, Sm, Eu, Gd, Tb, Dy, Ho, Er, Tm, Yb, or Lu.

24. The composition according to claim 18, wherein the ionic compound is a non-metallic organic salt which is an ammonium salt which is benzyltrimethylammonium, isobutylammonium, butyltrimethylammonium, decyltrimethylammonium, di-ethylammonium, dimethylammonium, dipropylammonium, dodecylammonium, dodecyltrimethylammonium, ethanol-ammonium, ethylammonium, ethyltrimethylammonium, or diammonium salt.

25. The composition according to claim 17, wherein the ionic compound is present in a concentration ranging from 0.001 to 25% by weight relative to the total weight of the composition.

26. The composition according to claim 25, wherein the concentration of the ionic compound ranges from 0.01 to 10% by weight.

27. The composition according to claim 25, wherein the concentration of the ionic compound ranges from 0.1 to 5% by weight.

28. The composition according to claim 1, wherein the composition further contains at least one direct dye which is a neutral, acid or basic direct nitrobenzene dye, a neutral, acid or basic direct azoic dye, a direct quinone dye, a direct azine dye, a direct methine dye, a direct triarylmethane dye, a direct indoamine dye or a direct natural dye.

29. The composition according to claim 28, wherein the direct quinone dye is a neutral, acid or basic anthraquinone dye.

30. The composition according to claim 28, wherein the direct dye is present in a quantity ranging from 0.001% to 10% by weight relative to the total weight of the composition.

31. The composition according to claim 1, wherein the composition further contains at least one oxidation base which is a para-phenylenediamine, a bis-phenylalkylenediamine, a para-aminophenol, an orthoaminophenol or a heterocyclic base.

32. The composition according to claim 31, wherein the oxidation base is present in a quantity ranging from 0.001 to 10% by weight relative to the total weight of the composition.

33. The composition according to claim 31, wherein the composition further contains at least one coupler which is a metaphenylenediamine, metaaminophenol, metadiphenol, naphthalene coupler or heterocyclic coupler.

34. The composition according to claim 33, wherein the coupler is present in a quantity ranging from 0.001 to 10% by weight relative to the total weight of the composition.

35. The composition according to claim 1, wherein the composition further contains at least one oxidizing agent.

36. The composition according to claim 35, wherein the oxidizing agent is hydrogen peroxide, urea peroxide, a bromate of an alkaline metal, a persalt, a peracid, or an enzyme.

37. The composition according to claim 36, wherein the persalt is a perborate or persulphate.

38. The composition according to claim 36, wherein the enzyme is a peroxydase, 2-electron oxido-reductase or 4-electron oxygenase.

39. A method for dyeing human keratin fibres, comprising applying to said human keratin fibres a composition containing at least one compound which is a chromoionophore or fluoroionophore for a length of time sufficient to develop a desired colour, the compound being made up of at least one ionophore molecule covalently bound to at least one chromophore or fluorophore molecule.

40. The method for dyeing human keratin fibres according to claim 39, wherein the composition further comprises an ionic compound.

41. The method for dyeing human keratin fibres according to claim 39, wherein a composition containing at least one ionic compound is subsequently applied to said human keratin fibres.

42. The method for dyeing human keratin fibres according to claim 39, wherein a composition containing at least one ionic compound is previously applied to said human keratin fibres.

43. The method for dyeing human keratin fibres according to claim 40, wherein the ionic compound is an inorganic metal salt of an alkaline metal, an alkaline earth metal, a transition metal, a rare earth metal or an alloy thereof, and the non-metallic organic salt is an ammonium salt which is benzyltrimethylammonium, isobutylammonium, butyltrimethylammonium, decyltrimethylammonium, di-ethylammonium, dimethylammonium, dipropylammonium, dodecylammonium, dodecyltrimethylammonium, ethanolammonium, ethylammonium, ethyltrimethylammonium, or diammonium salt.

44. The method for dyeing human keratin fibres according to claim 43, wherein the alkaline metal is Li, Na, K, or Cs.

45. The method for dyeing human keratin fibres according to claim 43, wherein the alkaline earth metal is Be, Mg, Ca, Sr, or Ba.

46. The method for dyeing human keratin fibres according to claim 43, wherein the transition metal is Sc, Ti, V, Cr, Mn, Fe, Co, Ni, Cu, Zn, Y, Zr, Nb, Mo, Tc, Ru, Rh, Pd, Ag, La, Cd, Hf, Ta, W, Re Os, Ir, Pt, or Au.

47. The method for dyeing human keratin fibres according to claim 43, wherein the rare earth metal is Ce, Pr, Nd, Pm, Sm, Eu, Gd, Tb, Dy, Ho, Er, Tm, Yb, or Lu.

48. A device or "kit" with several compartments for dyeing human keratin fibres comprising at least two compartments, one of which contains a composition containing, in a medium for dyeing human keratin fibres, at least one compound which is a chromoionophore or fluoroionophore, and the other of which contains a composition containing at least one ionic compound.

49. The method according to claim 39, wherein the chromophore or fluorophore molecule is a direct dye.

50. The method according to claim 49, wherein the chromophore or fluorophore molecule is a direct dye containing at least one cycloaliphatic, aromatic or heterocyclic cycle, and wherein the molecule does not contain more than four condensed cycles.

51. The method according to claim 49, wherein the chromophore or fluorophore is a molecule which is a neutral, acid or basic direct nitrobenzene dye, a neutral, acid or basic direct azoic dye, a direct quinone dye, a direct azine dye, a direct methine dye, a direct triarylmethane dye, a direct indoamine dye, or a direct natural dye.

52. The method according to claim 39, wherein the ionophore molecule is a chelatant, a podand, a coronand or a cryptand.

* * * * *